(12) United States Patent
Zhan et al.

(10) Patent No.: US 10,864,012 B2
(45) Date of Patent: Dec. 15, 2020

(54) TOOL BIT FOR ULTRASONIC OSTEOTOME AND ULTRASONIC OSTEOTOME HAVING THE SAME

(71) Applicant: Beijing SMTP Technology Co., Ltd., Beijing (CN)

(72) Inventors: Songtao Zhan, Beijing (CN); Chunyuan Li, Beijing (CN)

(73) Assignee: BEIJING SMTP TECHNOLOGY CO., LTD., Beijing (CN)

( * ) Notice: Subject to any disclaimer, the term of this patent is extended or adjusted under 35 U.S.C. 154(b) by 177 days.

(21) Appl. No.: 15/986,254

(22) Filed: May 22, 2018

(65) Prior Publication Data

US 2018/0263635 A1 Sep. 20, 2018

Related U.S. Application Data

(63) Continuation of application No. PCT/CN2016/106702, filed on Nov. 22, 2016.

(30) Foreign Application Priority Data

Nov. 23, 2015 (CN) .................... 2015 2 0935886 U

(51) Int. Cl.
*A61B 17/32* (2006.01)
*A61B 17/14* (2006.01)
*A61B 17/16* (2006.01)

(52) U.S. Cl.
CPC .... *A61B 17/320068* (2013.01); *A61B 17/144* (2016.11); *A61B 17/16* (2013.01);
(Continued)

(58) Field of Classification Search
CPC ....... A61B 17/14; A61B 17/144; A61B 17/16; A61B 17/32; A61B 17/320068; A61B 2017/320075; A61B 2017/320077
See application file for complete search history.

(56) References Cited

U.S. PATENT DOCUMENTS 4,036,236 A 7/1977 Rhodes, Jr.
5,188,102 A * 2/1993 Idemoto ......... A61B 17/320068
604/22

(Continued)

FOREIGN PATENT DOCUMENTS

CN 101141923 A 3/2008
CN 102697569 A 10/2012
(Continued)

OTHER PUBLICATIONS

International Search Report for PCT Application No. PCT/CN2016/106702; State Intellectual Property Office of the P.R. China; Beijing, China; dated Apr. 17, 2017.

(Continued)

*Primary Examiner* — Larry E Waggle, Jr.
(74) *Attorney, Agent, or Firm* — Thomas E. Lees, LLC

(57) ABSTRACT

A tool bit for an ultrasonic osteotome includes a bit body, an arbor fixed to the bit body, and a flat end portion fixed to the arbor. A toothed edge extends linearly along a length direction of an end portion of the tool bit, and recesses are distributed evenly on the toothed edge to form teeth spaced apart from each other. The toothed edge extends linearly along a length direction, and the cutting edges of teeth are distributed linearly, e.g., instead of having a sharp structure, thus will not scrape and hurt other tissues during cutting. Since the thickness of the cutting edge is the same as that of the back edge, when cutting bone tissues, the incision is wide, thus the end portion is not easy to be clamped by bone tissue, which effectively prevents the end portion from breaking and reduces occurrence chances of surgery accidents.

11 Claims, 4 Drawing Sheets

(52) U.S. Cl.
CPC .. *A61B 17/32* (2013.01); *A61B 2017/320075* (2017.08); *A61B 2017/320077* (2017.08)

(56) References Cited

U.S. PATENT DOCUMENTS

| | | | |
|---|---|---|---|
| 10,076,350 B2* | 9/2018 | Cao | A61B 17/1659 |
| 2008/0188878 A1 | 8/2008 | Young | |
| 2011/0125174 A1* | 5/2011 | Babaev | A61B 17/144 606/169 |
| 2013/0204255 A1 | 8/2013 | Milburn et al. | |
| 2015/0005771 A1* | 1/2015 | Voic | A61B 17/14 606/79 |

FOREIGN PATENT DOCUMENTS

| | | |
|---|---|---|
| CN | 202920294 U | 5/2013 |
| CN | 203354613 U | 12/2013 |
| CN | 205234577 U | 5/2016 |
| CN | 205831876 U | 12/2016 |
| EP | 3025660 A1 | 6/2016 |
| SU | 1225542 A1 | 4/1986 |
| WO | 2007065043 A1 | 6/2007 |
| WO | 2015/010506 A1 | 1/2015 |
| WO | 2015/132401 A1 | 9/2015 |
| WO | WO-2015132401 A1 * | 9/2015 ......... A61B 17/1659 |

OTHER PUBLICATIONS

Written Opinion of the International Searching Authority for PCT Application No. PCT/CN2016/106702; State Intellectual Property Office of the P.R. China; Beijing, China; dated Apr. 17, 2017.

International Preliminary Report on Patentability for PCT Application No. PCT/ CN2016/106702; The International Bureau of WIPO; Geneva, Switzerland; dated May 29, 2018.

European Search Report for European Patent Application No. 16867945.4; European Patent Office; Munich, Germany; dated Jul. 12, 2019.

Australian Examination Report No. 1 for Australian Patent Application No. 2016358787; Australian Government; IP Australia; dated May 29, 2019.

Australian Examination Report No. 2 for Australian Patent Application No. 2016358787; Australian Government; IP Australia; dated Sep. 30, 2019.

* cited by examiner

US 10,864,012 B2

TOOL BIT FOR ULTRASONIC OSTEOTOME AND ULTRASONIC OSTEOTOME HAVING THE SAME

CROSS REFERENCE TO RELATED APPLICATIONS

This is a Continuation application of International Application Serial No. PCT/CN2016/106702, filed on Nov. 22, 2016, which claims the benefit of Chinese Application No. 201520935886.9, filed on Nov. 23, 2015, the disclosures of which are hereby incorporated by reference.

BACKGROUND

The present disclosure relates to the field of mechanical instruments and devices, and in particular, to a tool bit for an ultrasonic osteotome and an ultrasonic osteotome having the same.

In an orthopedic surgery, an ultrasonic osteotome is often used to perform cutting, grinding, planing, scraping or arbitrary shaping on bones. A conventional tool bit for an ultrasonic osteotome has a plurality of teeth and has a long tip portion, and the teeth of the tip portion are distributed on a curved surface of the tip portion.

Such a tool bit for an ultrasonic osteotome involves problems including: the cutting force is applied downward with a large amount, which may cause a blunt injury easily; the tool bit is easy to be clamped by bone tissues and be broken, resulting in a short service life; the tool bit has a complicated shape and is difficult for machining, thus has a high manufacture cost.

BRIEF SUMMARY

The present disclosure has been made to overcome or alleviate at least one aspect of the above mentioned disadvantages. According to an aspect of the present invention, there is provided a tool bit for an ultrasonic osteotome comprising a bit body connected with an ultrasonic equipment, an arbor connected with the bit body, and a flat and straight end portion connected with the arbor. The end portion includes a toothed edge extending linearly along a length direction of the end portion, and a plurality of recesses are distributed evenly on the toothed edge to form teeth spaced apart from each other.

Preferably, the end portion further comprises a back edge, the back edge having an arcuate edge portion adjacent to a terminal of the end portion along a length direction thereof, and the arcuate edge portion is smoothly connected to the toothed edge.

Preferably, a thickness of cutting edges of the teeth is the same as a thickness of the back edge.

Preferably, there is a smooth curved connection between the end portion and the arbor.

Preferably, there are four recesses.

Preferably, a liquid guiding groove is formed on a side wall of the end portion along the length direction of the end portion.

Preferably, there are liquid guiding grooves disposed symmetrically on two side walls of the end portion.

Preferably, the liquid guiding groove is formed as a long hole penetrating through the two side walls of the end portion.

Preferably, a terminal end of the cutting edge of the tooth, in the length direction of the end portion, forms a rounded corner structure toward a root portion of the tooth.

Another aspect of the present disclosure also provides an ultrasonic osteotome comprising the tool bit for an ultrasonic osteotome as set forth above.

In comparison with the prior art, embodiments of the present disclosure have the following advantages: since the toothed edge on the end portion extends linearly along the length direction of the end portion, the cutting edges of the teeth are distributed linearly instead of having a sharp structure, thus will not scrape and hurt other tissues during cutting; since the thickness of the cutting edge is set to be the same as that of the back edge, when cutting bone tissues, the incision is wide and thus the end portion is not easy to be clamped by the bone tissues, which effectively prevents the end portion from breaking and reduces occurrence chances of surgery accidents.

BRIEF DESCRIPTION OF THE SEVERAL VIEWS OF THE DRAWINGS

In order to clearly describe the embodiments of the disclosure or the prior art, a brief description of the drawings used in describing the embodiments of the present disclosure or the prior art will be made. Apparently, the drawings provided only show some embodiments of the present disclosure. For those skilled in the art, other drawings may be obtained according to the disclosed drawings without inventive labor.

LIST OF REFERENCE NUMERALS

| 1-bit body | 2-arbor | 3-end portion of tool bit |
| 4-toothed edge | 5-recess | 6-tooth 7-back edge |
| 8-arcuate edge portion | 9-liquid guiding groove | |

DETAILED DESCRIPTION

Exemplary embodiments of the present disclosure will be described hereinafter clearly and completely with reference to the attached drawings. Apparently, the embodiments described herein are only portions of embodiments of the disclosure, rather than all embodiments of the disclosure. It is intended that all other embodiments obtained by those skilled in the art according to the disclosed embodiments without inventive labor are within the scope of the present invention.

In the description of the present disclosure, it is to be noted that the terms of "center", "upper", "lower", "left", "right", "vertical", "horizontal", "internal", "external" and the like simply indicate orientational or positional relationship based on the accompanying drawings and are used only for the purpose of facilitating and simplifying the description of the invention, rather than specifying or implying that any device or elements indicated must have a certain orientation, constitute with a certain orientation, or operate in a certain orientation. Therefore, these terms will not be interpreted as limiting the present invention. Further, the terms of "first", "second" and "third" are only used for describing purpose, rather than being interpreted as specifying or implying relative importance.

In the description of the present disclosure, it is to be noted that, unless otherwise specified or defined clearly, the term of "attach", "connect to", "connect with", "couple" and the like should be interpreted broadly. For example, they may refer to fixed connection, or detachable connection, or integral connection; they may refer to mechanical connection, or electrical connection; they may refer to direct connection, or indirect connection through an intermediate agent, or internal communication between two components. For those skilled in the art, the specific meaning of these terms in the present disclosure may be understood in combination with specific situations or contexts. In the following, the present invention will be described in detail by way of exemplary embodiments in combination with accompanying drawings.

Figure 2:
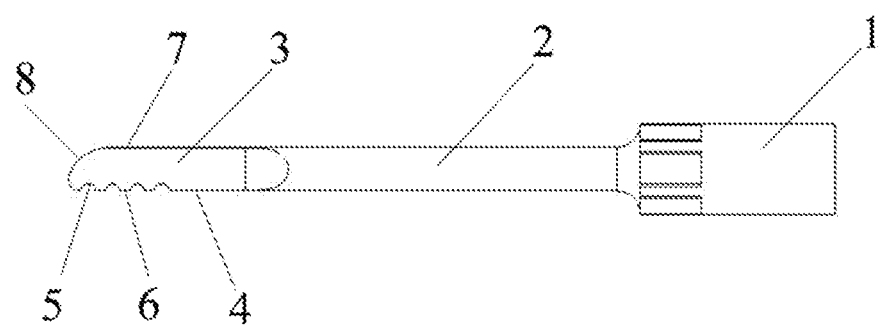
FIG. 2 is a schematic structural view of a tool bit for an ultrasonic osteotome according to an embodiment of the present disclosure.

As shown in FIG. 2, an embodiment of the present invention provides a tool bit for an ultrasonic osteotome, comprising a bit body 1 connected with an ultrasonic equipment, an arbor 2 fixedly connected with bit body 1, and a flat end portion 3 of the tool bit fixedly connected with arbor 2. End portion 3 of the tool bit includes a toothed edge 4 extending linearly along a length direction of end portion 3 of the tool bit, and a plurality of recesses 5 are distributed evenly on toothed edge 4 to form teeth 6 spaced apart from each other.

Figure 1:
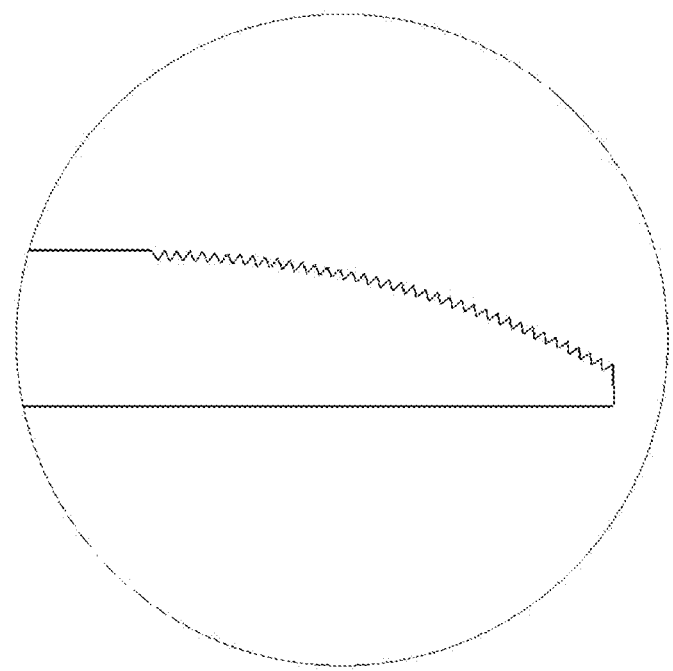
FIG. 1 is a schematic structural view of a tool bit for an ultrasonic osteotome according to prior art.

In the prior art, as shown in FIG. 1, an ultrasonic osteotome typically has an arcuate curved blade edge, and the blade edge also has sharp teeth. In an actual surgery operation, the sharp teeth structure may easily contact and scrape other tissues during cutting, which will hurt other tissues and cause medical accidents.

According to an embodiment of the present invention, since toothed edge 4 is provided on one side of end portion 3 of the tool bit, and toothed edge 4 extends linearly, that is, toothed edge 4 is a straight edge; and recesses 5 form and separate teeth 6, thus the cutting edges of the teeth 6 also have a linear distribution structure. Therefore, there are no sharp tooth structure, thus effectively reduces a risk of scraping other tissues and prevents medical accidents. Teeth 6 only perform cutting on a bone tissue. Other portions which do not contact bone tissues do not have sharp edges, thus will not hurt other tissues during a surgery operation, so that a surgeon can concentrate on the cutting of bone tissues, and the time for performing a surgery operation can be saved.

According to a specific design, four recesses 5 may be provided. Depending on different lengths of end portion 3 of the tool bit, various numbers of recesses 5 can be provided. Furthermore, an arcuate transition may be provided between arbor 2 and bit body 1. Bit body 1 may have connection threads on the other end thereof. The connection threads may be disposed internally. Bit body 1 may be provided with a regular hexagon portion for a wrench. When the connection threads of bit body 1 are connected to a specific ultrasonic transducer and screwed tightly with a suitable wrench, and then the ultrasonic transducer are connected to a specific ultrasonic main machine, the ultrasonic osteotome comes into operation.

In an embodiment of the invention, the end portion of the tool bit further comprises a back edge 7. Back edge 7 has an arcuate edge portion 8 formed adjacent to a terminal of end portion 3 of the tool bit along a length direction thereof, and arcuate edge portion 8 is smoothly connected to toothed edge 4.

Back edge 7 is formed with arcuate edge portion 8 being adjacent to a terminal of the end portion 3 of the tool bit along a length direction thereof, then end portion 3 of the tool bit have a smooth curved surface at the end thereof. Therefore, when end portion 3 of the tool bit is inserted into a wound, due to said terminal of the end portion of the tool bit being smooth, the damage to other tissues can be avoided. That is to say, there is no sharp corner angle hooking other tissues on the way, so that any hurt can be avoided and the safety of the surgery can be improved.

Figure 3:
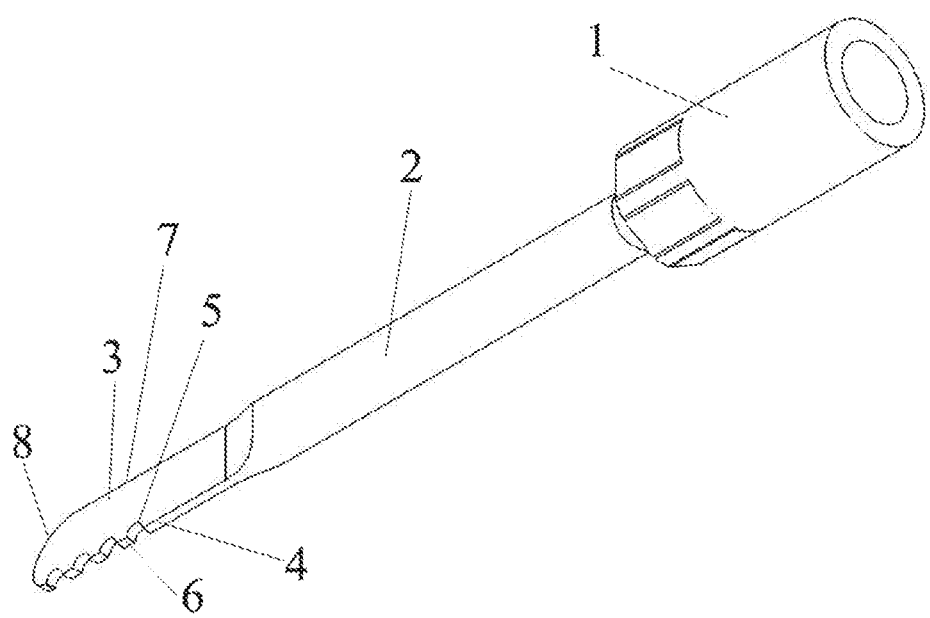
FIG. 3 is a schematic perspective structural view of a tool bit for an ultrasonic osteotome according to an embodiment of the present disclosure.

As shown in FIG. 3, in an embodiment of the present invention, the thickness of cutting edges of teeth 6 is identical to the thickness of back edge 7.

Since cutting edges of teeth 6 are designed to have a certain thickness, in the case of cutting a bone tissue, the width of a incision will be increased. Because the incision has a certain thickness, end portion 3 of the tool bit will not be clamped by the incision during cutting with the increase of the cutting depth. The defect of the prior art lies in that the end portion of the tool bit is very thin and thus the end portion of the tool bit will be embedded in the incision with the increase of the cutting depth, and even be broken in severe case. Embodiments of the present invention avoid such phenomenon in that a wider cutting edge permits end portion 3 of the tool bit to have sufficient space to move, and thus effectively avoid breaks of end portion 3 of the tool bit.

Furthermore, in an embodiment of the present invention, a smooth connection is provided between end portion 3 of the tool bit and arbor 2.

For the reason that a smooth connection is provided between end portion 3 of the tool bit and arbor 2, scraping phenomenon can be avoided when arbor 2 is extruded into a tissue.

Figure 4:
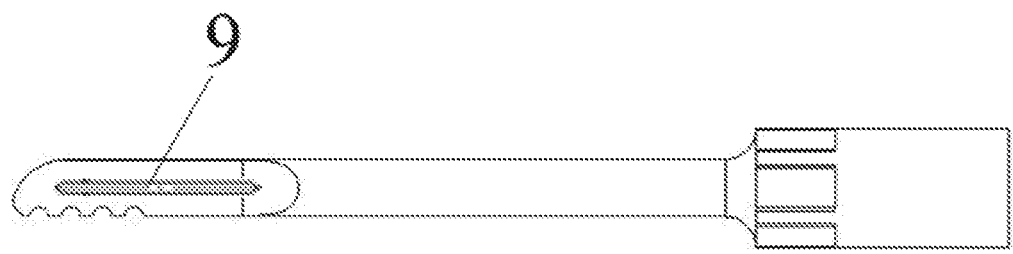
FIG. 4 is a schematic structural view of a tool bit for an ultrasonic osteotome with a liquid guiding groove according to an embodiment of the present disclosure.

As shown in FIG. 4, in an embodiment of the present invention, a liquid guiding groove 9 is formed on a side wall of end portion 3 of the tool bit along the length direction of end portion 3 of the tool bit.

Liquid guiding groove 9 is provided for the intention that a knife handle can spray water on a cutting portion to reduce the temperature and to clean the incision, during the process of cutting a bone tissue. Liquid guiding groove 9 can effectively guide water toward end portion 3 of the tool bit so as to reduce the temperature. Guided by liquid guiding groove 9, the water stream reduces the temperature firstly and then flushes the left debris in the incision, so that the cutting portion can be kept clean and an operator can watch the cutting state timely, resulting in the accuracy of the surgery being improved.

Certainly, when liquid guiding grooves 9 are provided symmetrically on two side walls of end portion 3 of the tool bit so as to guide water stream from two sides, both the effect of temperature reducing resulted from end portion 3 of the tool bit and the effect of water stream cleaning can be improved further.

Furthermore, liquid guiding groove 9 may be formed as a long hole penetrating through two side walls of end portion 3 of the tool bit. In an actual application, such a long hole penetrating through the body of end portion 3 of the tool bit can distribute water stream toward two sides of end portion 3 of the tool bit via the long hole, thus water can be sprayed only from one side of end portion 3 of the tool bit and only one water spraying mechanism being necessary to be provided on the knife handle, which saves manufacture cost.

Figure 5:
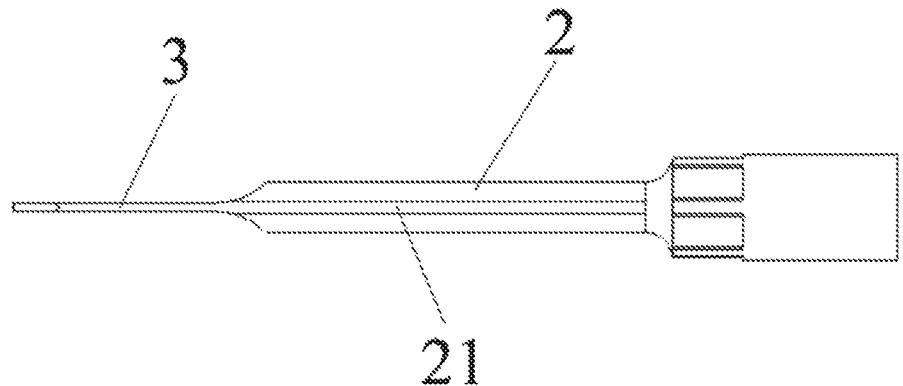
FIG. 5 is a first schematic structural view of an arbor with a water stream channel according to an embodiment of the present disclosure.

Further, as shown in FIG. 5, in an embodiment of the present invention, a water stream channel 21 can be provided within the arbor 2. One end of water stream channel 21 starts from an inside wall of bit body 1 at a connection portion between the bit body and an ultrasonic handle, and the other end thereof is in a direct communication to the inner wall of the long hole, so that water can be sprayed toward the cutting portion through the long hole, then both the temperature reduction of end portion 3 of the tool bit and the cleaning of the cutting portion can be realized.

Figure 6:
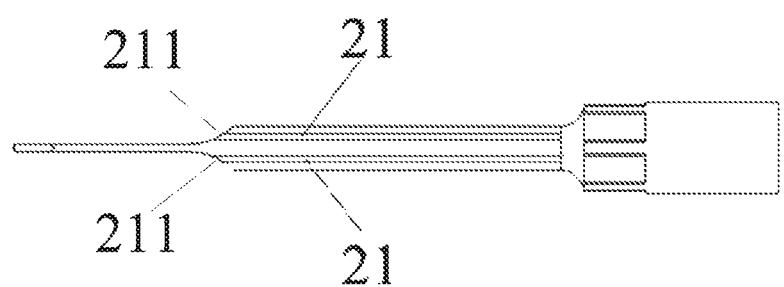
FIG. 6 is a second schematic structural view of an arbor with a water stream channel according to an embodiment of the present disclosure.

As shown in FIG. 6, two water stream channels 21 can be formed within the arbor 2 with water outlets 211 being provided at both sides of end portion 3 of the tool bit, so as to reduce the temperature of end portion 3 of the tool bit and to clean the cutting portion from two sides respectively.

Figure 7:
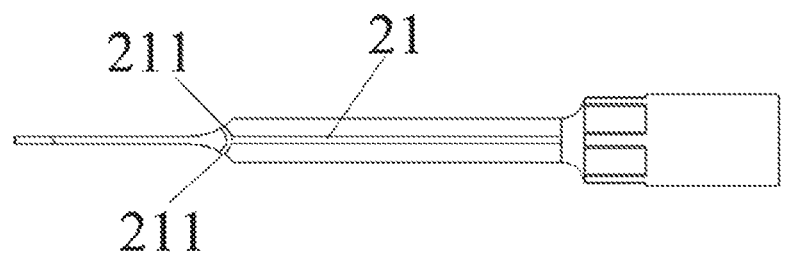
FIG. 7 is a third schematic structural view of an arbor with a water stream channel according to an embodiment of the present disclosure.
Figure 8:
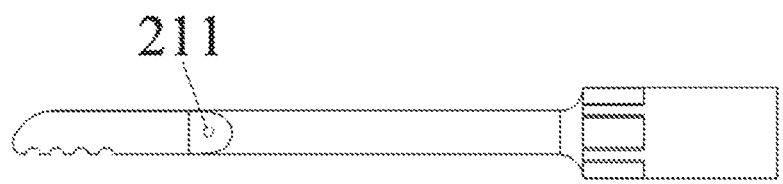
FIG. 8 is a schematic structural view of a water outlet for an arbor according to an embodiment of the present disclosure.

Certainly, as shown in FIG. 7, it is also possible to provide one water stream channel, but the one water stream channel is branched toward two sides at a position adjacent to end portion 3 of the tool bit, so as to form two water outlets 211 to reduce the temperature of end portion 3 of the tool bit and to clean the cutting portion from two sides respectively. The external structure of water outlet 211 is shown in FIG. 8.

Furthermore, the arbor can be lengthened further or curved in a certain degree so that the operator can insert the end portion of the tool bit deep into an interior of a wound during operation, then the operation can be simplified and the difficulty of a surgery can be reduced.

In an embodiment of the present invention, a terminal end of the cutting edge of tooth 6 along the length direction of end portion 3 of the tool bit forms a rounded corner structure towards a root portion of tooth 6.

The rounded corner structure is provided with the intention to further prevent teeth 6 from cutting other tissues by mistake. The rounded corner structure can effectively avoid soft tissue from being scraped, and can guarantee that teeth 6 performs cutting directly on a bone tissue.

The present disclosure also provides an ultrasonic osteotome comprising the tool bit for an ultrasonic osteotome as set forth in the above embodiments.

In the present invention, the tool bit for an ultrasonic osteotome can concentrate all energy generated by an ultrasonic transducer on end portion 3 of the tool bit, so that end portion 3 of the tool bit of the scalpel owns a strongest energy output and achieves highest working effect to cut a bone tissue effectively. That the back edge 7 has an arcuate edge portion adjacent to a terminal of end portion 3 of the tool bit in an extending direction thereof can prevent tissues being scraped and being injured by a sharp end, so that the safety of a surgery can be improved.

It should be noted that the above embodiments are only used to describe the concept of the present invention, rather than limiting the present invention. Although detailed descriptions of the invention are made with reference to the above embodiments, it would be appreciated by those skilled in the art that various changes or modifications to the above embodiments can be made or equivalent substitutions to partial or all features in those embodiments can be made. Such changes, modifications or substitutions will not make the spirit of the relevant solutions depart from the scope of the present invention, which is defined in the claims and their equivalents.

What is claimed is:

1. A tool bit for an ultrasonic osteotome, comprising:
a bit body connected with an ultrasonic equipment;
an arbor fixed to the bit body; and
a flat end portion of the tool bit fixed to the arbor;
wherein an end portion of the tool bit includes a toothed edge extending linearly along a length direction of the end portion of the tool bit, wherein the tool bit further comprises:
a plurality of recesses which are distributed evenly on the toothed edge to form teeth spaced apart from each other, wherein cutting edges of the teeth have a linear distribution structure and overlap with an extension of the toothed edge such that the cutting edges of the teeth are not formed with sharp tooth structure,
wherein the end portion of the tool bit further comprises a back edge having an arcuate edge portion adjacent to a terminal of the end portion of the tool bit in a length direction thereof, and wherein the arcuate edge portion is smoothly connected to the toothed edge, and
wherein a thickness of cutting edges of the teeth is the same as a thickness of the back edge.

2. The tool bit for an ultrasonic osteotome according to claim 1, wherein there is a smooth curved connection between the end portion of the tool bit and the arbor.

3. The tool bit for an ultrasonic osteotome according to claim 2, wherein there are four recesses.

4. The tool bit for an ultrasonic osteotome according to claim 3, wherein:
a liquid guiding groove is formed on a side wall of the end portion of the tool bit along the length direction of the end portion of the tool bit.

5. The tool bit for an ultrasonic osteotome according to claim 3, wherein:
the end portion includes a first side wall and a second side wall;
a first liquid guiding groove is formed on the first side wall along the length direction of the end portion of the tool bit;
a second liquid guiding groove is formed on the second side wall along the length direction of the end portion of the tool bit; and
the first liquid guiding groove and the second liquid guiding groove are disposed on the tool bit symmetrically.

6. The tool bit for an ultrasonic osteotome according to claim 3, wherein:
the end portion has two side walls including a first side wall and a second side wall;
a liquid guiding groove is formed as a long hole penetrating through the two side walls along the length direction of the end portion of the tool bit.

7. The tool bit for an ultrasonic osteotome according to claim 1, wherein there is a smooth curved connection between the end portion of the tool bit and the arbor.

8. The tool bit for an ultrasonic osteotome according to claim 1, wherein there are four recesses.

9. The tool bit for an ultrasonic osteotome according to claim 1, wherein:

a liquid guiding groove is formed on a side wall of the end portion of the tool bit along the length direction of the end portion of the tool bit.

10. The tool bit for an ultrasonic osteotome according to claim 1, wherein:
   the end portion includes a first side wall and a second side wall;
   a first liquid guiding groove is formed on the first side wall along the length direction of the end portion of the tool bit;
   a second liquid guiding groove is formed on the second side wall along the length direction of the end portion of the tool bit; and
   the first liquid guiding groove and the second liquid guiding groove are disposed on the tool bit symmetrically.

11. The tool bit for an ultrasonic osteotome according to claim 1, wherein:
   the end portion has two side walls including a first side wall and a second side wall;
   a liquid guiding groove is formed as a long hole penetrating through the two side walls along the length direction of the end portion of the tool bit.

* * * * *